US007022133B2

(12) United States Patent
Yee et al.

(10) Patent No.: US 7,022,133 B2
(45) Date of Patent: Apr. 4, 2006

(54) MULTI-SHEATH DELIVERY CATHETER

(75) Inventors: Carl E. Yee, Austin, TX (US); Thomas Roberts, Mountain Lakes, NJ (US); Frank Occidentale, Elmwood Park, NJ (US); Robert Christie, Manchester, CT (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/457,183

(22) Filed: Jun. 9, 2003

(65) Prior Publication Data

US 2003/0199916 A1 Oct. 23, 2003

Related U.S. Application Data

(60) Continuation of application No. 09/894,426, filed on Jun. 28, 2001, now Pat. No. 6,589,251, which is a division of application No. 08/970,541, filed on Nov. 14, 1997, now abandoned.

(51) Int. Cl.
*A61F 2/06* (2006.01)
(52) U.S. Cl. ................ 623/1.11; 623/1.23; 606/108
(58) Field of Classification Search ................ 606/1, 606/108, 159, 171, 191–200, 213; 604/96.01–109, 604/64.01, 171, 264, 523–539, 284, 158, 604/159; 623/1.1, 1.11, 1.13, 1.15, 1.16, 623/1.23, 1.35, 2.11, 11.11, 902, 903, 904
See application file for complete search history.

(56) References Cited

U.S. PATENT DOCUMENTS 4,665,918 A * 5/1987 Garza et al. ................ 606/108

| 4,682,981 A | | 7/1987 | Suzuki et al. |
| 5,290,310 A | * | 3/1994 | Makower et al. ........... 606/213 |
| 5,405,377 A | | 4/1995 | Cragg |
| 5,571,168 A | | 11/1996 | Toro |
| 5,609,627 A | | 3/1997 | Goicoechea et al. |

(Continued)

FOREIGN PATENT DOCUMENTS

EP 0 364 420 A1 4/1990

OTHER PUBLICATIONS

Communication with Supplementary Partial European Search Report for corresponding European Application No. EP 98 95 8554, mailed Sep. 29, 2003.

*Primary Examiner*—Glenn K. Dawson
(74) *Attorney, Agent, or Firm*—RatnerPrestia (57) ABSTRACT

A multi-sheath delivery catheter and method for introducing a prosthesis into a body lumen involving use of (a) an outer sheath adapted to contain a portion of the prosthesis and having an inner surface with a non-round cross-section; (b) a middle sheath slideably disposed at least partly within the outer sheath and adapted to contain another portion of the prosthesis, the middle sheath having a distal end with a first handle attached to it that has a non-round cross-section corresponding to and engaging the non-round cross-section of the inner surface of the outer sheath; and (c) a pusher slideably disposed at least partly within the middle sheath and adapted to engage the prosthesis, relative rotational movement between the outer sheath and the middle sheath is prevented by virtue of the engagement of the non-round cross-section of the first handle with the non-round cross-section of the inner surface of the outer sheath. The delivery catheter has a mechanism for sequentially retracting concentric tubes to deploy the prosthesis.

40 Claims, 8 Drawing Sheets

U.S. PATENT DOCUMENTS

| | | | |
|---|---|---|---|
| 5,690,644 A * | 11/1997 | Yurek et al. | 623/1.11 |
| 5,769,885 A | 6/1998 | Quiachon et al. | |
| 5,868,755 A | 2/1999 | Kanner et al. | |
| 6,071,279 A | 6/2000 | Whayne et al. | |
| 6,190,360 B1 | 2/2001 | Iancea et al. | |
| 6,589,251 B1 * | 7/2003 | Yee et al. | 606/108 |

* cited by examiner

MULTI-SHEATH DELIVERY CATHETER

CROSS-REFERENCE TO RELATED APPLICATIONS

This application is a continuation of U.S. patent application Ser. No. 09/894,426, filed Jun. 28, 2001, now U.S. Pat. No. 6,589,251 which is a divisional application of U.S. patent application Ser. No. 08/970,541, filed Nov. 14, 1997 (status: abandoned).

FIELD OF THE INVENTION

This invention relates to the deployment of endoluminal prostheses and, more particularly, to an improved multi-sheath delivery catheter for such deployment.

BACKGROUND OF THE INVENTION

Endoluminal prostheses are used for reinforcing or repairing blood vessels and other lumens within the body. For example, arteries narrowed or occluded by stenosis, thrombosis, or aneurysm may be reinforced, with or without additional surgical procedures such as angioplasty, by placing a prosthesis in the diseased portion of the artery. Such prostheses may be deployed within a body lumen by minimally invasive endoluminal insertion techniques. These include "surgical cut-down" procedures in which a small incision is made in the vasculature, for example in the femoral artery in the leg or in an artery in the shoulder of a patient, and a catheter is inserted at that location into the vessel. The catheter is maneuvered to the desired point of deployment, and the prosthesis is advanced through the catheter to that point. During this insertion process, the prosthesis is in a reduced diameter configuration, smaller than its intended diameter for use in repairing the vessel. The prosthesis is then expelled from the catheter into the vessel and expanded, with or without additional manipulation, into its intended use diameter within the vessel. The catheter is then removed from the body. Alternatively, percutaneous access may be used, wherein a needle puncture rather than a surgical incision is used to gain access to the vasculature. Percutaneous techniques are used for inserting relatively small prostheses; surgical cut-down techniques are used for relatively large ones.

A typical known insertion catheter consists of an outer sheath having a pusher slidably disposed within it. See, for example, U.S. Pat. No. 5,405,377 to Cragg. Once the catheter is inserted in the vessel and the prosthesis is advanced to the desired location within the vessel, the pusher is held in place while the outer sheath is retracted. This effectively discharges the prosthesis from the catheter.

For some prostheses, this simple pusher-in-sheath catheter arrangement is insufficient. An example of such a prosthesis is one having multiple diameters along its axis, such as the bifurcated prosthesis described in U.S. Pat. No. 5,609,627 to Goicoechea et al. The bifurcated prosthesis described in that patent has a stent portion having a first diameter adapted to be disposed in an aorta, and a branch portion having a second diameter, smaller than the first diameter, that extends into one of the iliac arteries. To insert such a multi-diameter stent, a multi-sheath delivery catheter is required.

It is also occasionally necessary to use a multi-sheath catheter to deliver a conventional straight prosthesis. With some prostheses, significant frictional forces exist between the prosthesis and the outer sheath of the catheter in which it is contained for transport to the delivery location and deployment. This may be the case with relatively long prostheses because friction increases as the outer surface area of the prosthesis increases.

Figures 1, 2, 3:
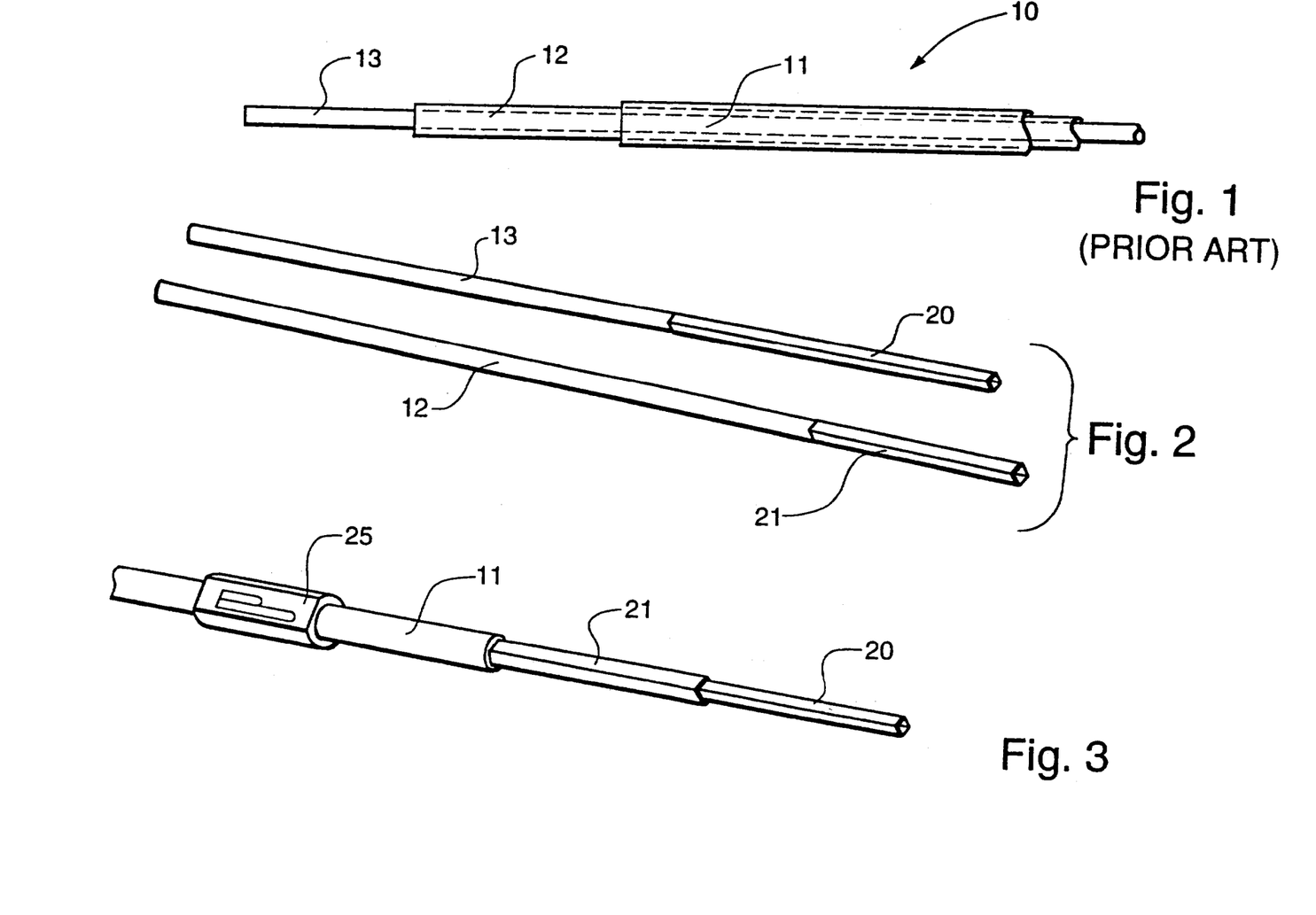
FIG. 1 is a side view of a portion of a prior art multi-sheath delivery catheter.
FIG. 2 is an isometric view of component portions of an exemplary multi-sheath delivery catheter according to this invention.
FIG. 3 is an isometric view of the component portions illustrated in FIG. 2 assembled into an exemplary multi-sheath delivery catheter according to this invention.

A known multi-sheath delivery catheter 10 is illustrated in FIG. 1. Multi-sheath catheter 10, similar to that disclosed in Goicoechea '627, comprises outer sheath 11, middle sheath 12, and pusher 13. Outer sheath 11 and middle sheath 12 are designed to be of an optimum diameter for containing the aortic portion and one bifurcated leg portion, respectively, of the bifurcated stent described above.

Outer sheath 11, middle sheath 12, and pusher 13 are concentrically slidably disposed relative to one another and are diametrically sized such that the prosthesis does not buckle against pusher 13 during deployment. In order to deploy a prosthesis contained within outer sheath 11 and middle sheath 12, catheter 10 is first percutaneously inserted to the desired delivery location within a body lumen according to methods known in the art. Outer sheath 11 is then retracted while middle sheath 12 and pusher 13 are held stationary. This action releases the first portion of the prosthesis that had been contained by outer sheath 11 because stationary middle sheath 12 and pusher 13 effectively prevent the first and second portions, respectively, of the prosthesis from moving as outer sheath 11 is retracted. Outer sheath 11 and middle sheath 12 are then retracted together while pusher 13 is held stationary to complete deployment of the prosthesis.

During this deployment, it is important that the tubes do not rotate with respect to one another. Rotation of any one of the tubes independently along its axis will not rotate the others. Such rotation could cause twisting or misalignment of the prosthesis being delivered. This also makes it difficult to gauge the twist or orientation of the prosthesis within the catheter, which is critical for aligning bifurcated prostheses with the anatomy. In addition, if the concentric tubes described above are not withdrawn in the proper order, the system will not properly deploy the prosthesis. Care must thus be exercised by a physician using a multi-sheath catheter to implant a prosthesis to retract the tubes in proper order.

An improved multi sheath delivery catheter for deployment of endoluminal prostheses is desired.

SUMMARY OF THE INVENTION

In a first aspect, the present invention provides a multi-sheath delivery catheter for introducing a prosthesis into a body lumen that has (a) an outer sheath adapted to contain a portion of the prosthesis and having an inner surface with a non-round cross-section; (b) a middle sheath slideably disposed at least partly within the outer sheath and adapted to contain another portion of the prosthesis, the middle sheath having a distal end with a first handle attached to it that has a non-round cross-section corresponding to and engaging the non-round cross-section of the inner surface of the outer sheath; and (c) a pusher slideably disposed at least partly within the middle sheath and adapted to engage the prosthesis; whereby relative rotational movement between the outer sheath and the middle sheath is prevented by virtue of the engagement of the non-round cross-section of the first handle with the non-round cross-section of the inner surface of the outer sheath. The pusher has a distal end with a second handle attached to it that has a non-round cross-section corresponding to and engaging the non-round cross-section of the first handle, whereby relative rotational movement between the pusher and the middle sheath is prevented by virtue of the engagement of the non-round cross-section of the second handle with the non-round cross-section of the first handle.

In another aspect, the invention provides a method for introducing a prosthesis to a body lumen using a multi-sheath delivery catheter having an outer sheath with an inner surface, a middle sheath having a distal end and being slideably disposed at least partly within said outer sheath, and a pusher having a distal end and being slideably disposed at least partly within said middle sheath. The method includes the steps of (a) forming a non-round cross-section in the inner surface of the outer sheath; and (b) attaching to the distal end of the middle sheath a handle that has a non-round cross-section corresponding to and engaging the non-round cross section formed in the inner surface of the outer sheath. The method also includes the step of attaching to the distal end of the pusher a handle that has a non-round cross-section corresponding to and engaging the non-round cross section of the middle sheath.

In another aspect, the invention provides a delivery catheter having a plurality of concentric tubes including an outer tube with an inner surface and an inner tube with an outer surface, at least one of which tubes is adapted to contain at least a portion of the prosthesis, and a first protrusion on the inner surface of the outer tube and a second protrusion, adapted to engage the first protrusion, on the outer surface of the inner tube, wherein the outer tube is adapted to be retracted over the inner tube before engagement of the first and second protuberances, and the outer tube and the inner tube are adapted to be retracted together upon the engagement.

In another aspect, the invention provides a delivery catheter having a plurality of concentric tubes including an outer tube having a distal end and an inner surface and an inner tube having a periphery, at least one of which tubes is adapted to contain at least a portion of the prosthesis during introduction to the body lumen, and (a) at least one notch on the inner tube; (b) a prong assembly disposed on the periphery of the inner tube and abutting the distal end of the outer tube, the prong assembly having at least one prong adapted to engage the notch in the inner tube; (c) a lock ring having a first portion adapted to be disposed over the distal end of the outer tube and a second portion adapted to be disposed over the prong assembly abutting the distal end; and (d) a protrusion on the inner surface of the outer tube; wherein the second portion of the lock ring is adapted to exert a force on the prong assembly sufficient to maintain the engagement of the prong with the notch and thereby prevent relative axial movement of the inner and outer tubes.

In another aspect, the invention provides a delivery catheter having a plurality of concentric tubes including an outer tube having a distal end and an inner tube having a periphery. The catheter also has (a) at least one notch on the inner tube; (b) a cam-lock assembly having (i) a hub fixedly attached to the distal end of the outer tube; and (ii) a cam-lock knob rotationally attached to the hub around the periphery of the inner tube; (iii) the cam-lock knob having a detailed inner cam surface adapted to engage the notch in a first position, thereby preventing relative axial motion between the inner and outer tubes, and disengaging the notch in a second position, thereby permitting relative axial motion between the inner and outer tubes.

In another aspect, the invention provides a delivery system for introducing a prosthesis to a body lumen including (a) a guidewire; (b) a catheter with a lumen adapted to slide over said guidewire, a proximal end, an interior, and a plurality of concentric tubes, at least one of which is adapted to contain at least a portion of the prosthesis during introduction to the body lumen; and (c) a nose cone disposed around the guide wire at the proximal end of the catheter, the nose cone having a hole formed through it that is adapted to communicate with both the interior of the catheter and an ambient environment before insertion of the nose cone into the body lumen; whereby the hole allows flushing of the catheter to remove air bubbles from the catheter before insertion into the body lumen.

In another aspect, this invention provides a method for preventing leakage of fluid from an interior of a delivery catheter by disposing the outer tube on a mandrel having a cross-sectional area substantially equivalent to that of the inner tube, applying a compressive force to a portion of the outer tube, heating the outer tube to shrink it around the mandrel, and assembling the outer tube concentrically over the inner tube such that a seal is created between the portion of the outer tube and the inner tube.

DETAILED DESCRIPTION OF THE INVENTION

As shown in FIG. 1 discussed above, the basic components of a known multi-sheath delivery catheter include an outer sheath 11, adapted to hold a first portion of a prosthesis to be delivered, a middle sheath 12, adapted to hold a second portion of the prosthesis to be delivered, and a pusher 13 for engaging, typically abutting, the distal end of the prosthesis contained within the catheter. Throughout this specification, the term "distal" shall mean "furthest from the heart," and the term "proximal" shall mean "closest to the heart." In addition, although two sheaths and one pusher are typically illustrated in the exemplary embodiments of the multi-sheath delivery catheter of this invention, additional sheaths or pushers may be included and are intended to be encompassed within the scope of the invention described herein. The sheaths and pushers may generally be referred to as tubes.

Figure 5:
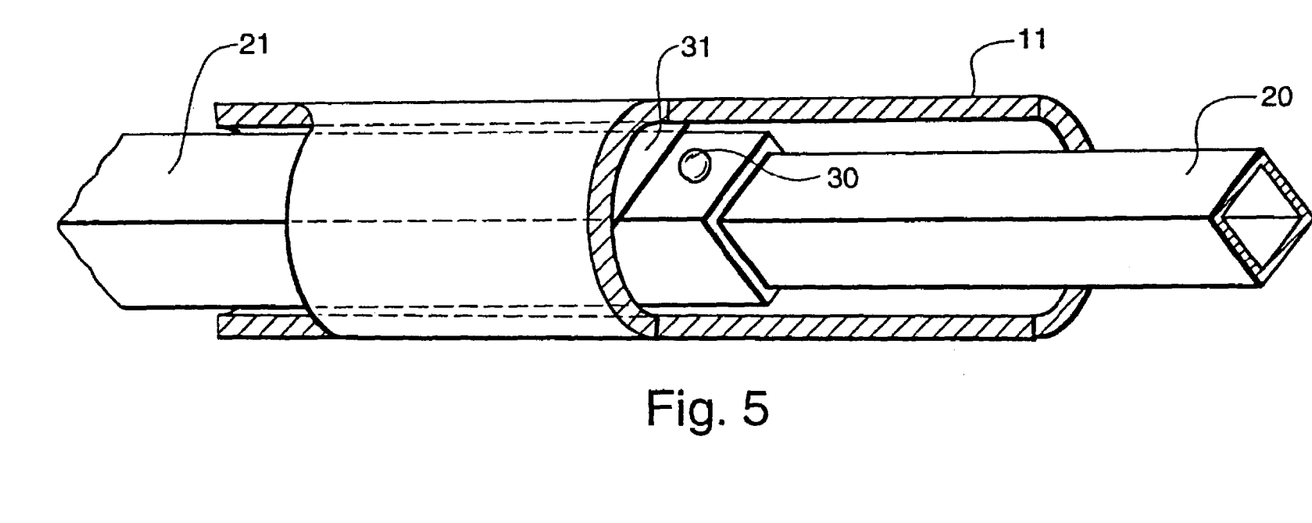
FIG. 5 is a partially cut-away isometric view of a portion of an exemplary multi-sheath delivery catheter according to this invention.

In a first aspect of this invention, the inventors have added features to a multi-sheath delivery catheter that prevent the sheaths and pusher from rotational motion relative to one another, while permitting the sheaths and pusher to slide axially relative to one another. As shown in FIG. 2, the anti-rotation feature involves attachment of a non-round profile handle 20 to pusher 13 and a non-round profile handle 21 to middle sheath 12. Preferably, handles 20 and 21 have the same non-round profile. The same non-round profile is also formed on at least a portion 31 (as shown in FIG. 5) of the inner surface of outer sheath 11. Non-round portion 31 may be integral with outer sheath 11 or formed by a separate member attached to it, such as by molding onto the inner surface. Alternatively, another non-round profile handle (not shown) may be attached to outer sheath 11 rather than forming the non-round profile on portion 31. In such an alternative embodiment, the handle is attached to outer sheath 11 as described below.

Figure 17A:
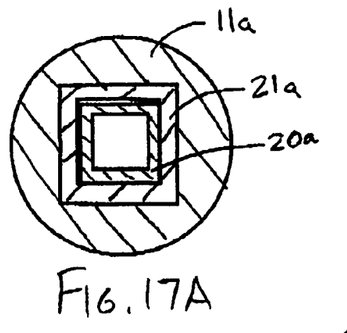
FIGS. 17A–F are cross-sectional views of exemplary multi-sheath delivery catheters having various cross-sectional profiles.
Figure 17B:
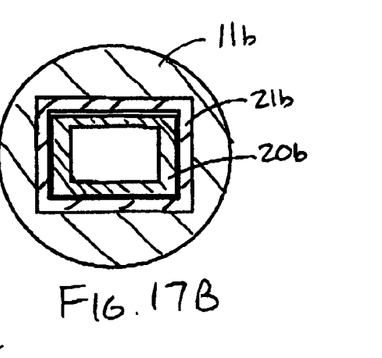
Figure 17C:
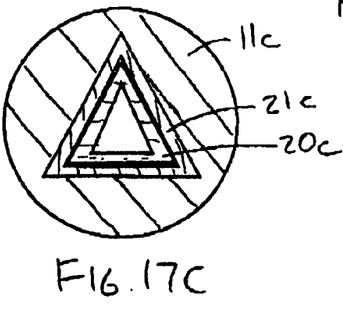
Figure 17D:
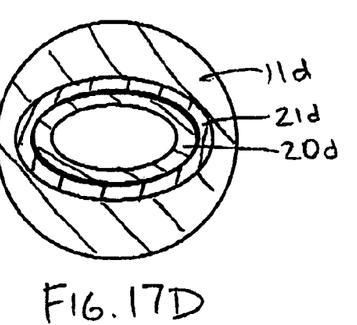
Figure 17E:
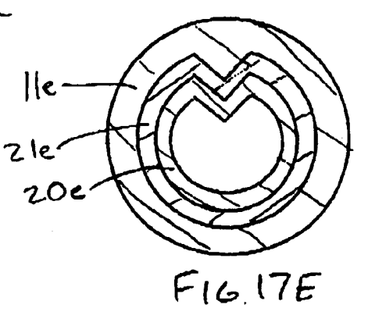
Figure 17F:
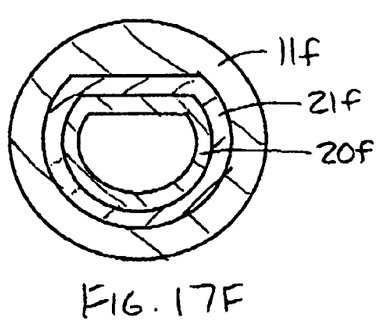

The non-round profile of handles 20 and 21 and of portion 31 on the inner surface of outer sheath 11 are shown in FIGS. 2-8 and FIG. 17A to be square. Any non-round profile for the inner surface of outer sheath and the profiles of handles 20 and 21 is suitable for purposes of this invention, however, as illustrated by exemplary inner sheaths 11a-f, handles 20a-20f, and handles 21a-21f, shown in cross-section in FIGS. 17A-17F, respectively. For instance, by way of example only, the non-round profile may be rectangular as shown in FIG. 17B; triangular as shown in FIG. 17C; ovular as shown in FIG. 17D; creased, such as the collapsed circle shown in FIG. 17E; or flattened, such as the D-shaped profile shown in FIG. 17F.

Preferably, handles 20 and 21 are formed of stainless steel and attached to pusher 13 and middle sheath 12, respectively, which are formed of polyethylene. To attach such stainless steel handles to polyethylene tubes, small notches are formed in the proximal end of the handle to be attached to the distal end of a tube. The proximal end of the handle is then inserted into the distal end of the tube and Teflon heat shrink tubing, known to those skilled in the art, is placed around the overlapping portions of the handle inside the tube. Upon heating, typically with a heat gun or a lap-welder, to a temperature and for a time period that may be easily optimized by those skilled in the art, the heat shrink tubing shrinks, thereby causing the tube to shrink down into tight engagement with the steel handle. In addition, the polyethylene of the tube melts and flows into the notches formed on the handle. Upon cooling this forms a tight interlocking bond between the tube and the handle. The heat shrink tubing may be removed and discarded.

Because pusher 13 typically has a very small internal diameter, it may be necessary to bore out the distal end of pusher 13 before insertion of handle 20 and attachment of the two as described above. Other modular attachment methods may also be used to attach handles 21 and 20 to middle sheath 12 and pusher 13, as will be understood by those skilled in the art.

FIG. 3 illustrates the multi-sheath catheter of this invention formed from the components of FIG. 2 which have been coaxially assembled. In the arrangement shown in FIG. 3, pusher 13 is contained within middle sheath 12, and handle 20 is contained within handle 21. All of the tubes and handles are contained within outer sheath 11. In one final configuration used by a physician to implant a prosthesis, tubular handle 21 attached to middle sheath 12 is entirely covered by outer sheath 11. Handle 20 may protrude from the distal end of outer sheath 11 for manipulation by the physician. In another final configuration, handle 21 may also protrude from the distal end of the outer sheath 11 for manipulation by the physician. The tubes are all dimensioned such that they can all slide axially with respect to one another but, because of the non-round profile of handles 20 and 21 and portion 31 of the inner surface of outer sheath 11, the tubes cannot rotate relative to one another. Rotation of any of the tubes cause the other tubes to rotate with it.

Another advantage of this invention is that non-round handles 20, 21 attached to pusher 13 and middle sheath 12, respectively, prevent pusher 13 from falling out of middle sheath 12 distally, and middle sheath 12 from falling out of outer sheath 111 distally.

A visual indicator 25 may optionally be added to the outside of outer sheath 11 (or anywhere else along the catheter handles adapted to remain outside the body into which the catheter is inserted) to illustrate the rotational orientation of the endoprosthesis within the delivery catheter. As shown in FIG. 3, the disposition of a "long leg-short leg" bifurcated endoprosthesis contained within the catheter is visually depicted. Absent such visual indicator 25, the only way to determine prosthesis orientation is by interpretation of the position of radiopaque markers using fluoroscopy. Visual indicator 25 allows the catheter to be introduced into the body in approximately the correct rotation, requiring less adjustment once inside the patient. Radiopaque markers may or may not be used in conjunction with this insertion.

The non-round profile of handle 20, which may be exposed to a physician, provides both tactile and visual feedback to the physician when the catheter is rotated. The described system makes deployment of the endoprosthesis easier and more controlled by adding stiffness and stability to the handle region where forces are applied. The coaxial handles 20 and 21 of the system maintain a low profile for the catheter and do not add unnecessary weight or bulk. Using the anti-rotation system described above prevents twisting of the endoprosthesis within the delivery catheter by preventing the sheaths from rotating relative to one another, thus preventing deployment of the prosthesis in a twisted configuration.

With a multi-sheath delivery catheter such as that described in connection with this invention, it is important that sheaths are withdrawn in the proper order. Otherwise, the system will not deploy the prosthesis. Accordingly, another aspect of this invention automatically ensures that the retraction of the tubes of the catheter during deployment of the prosthesis is performed in the proper sequence;

namely, outer sheath 11 is first retracted to release the first, typically larger, portion of the prosthesis, then middle sheath 12 retracted to release the second, typically smaller, portion. Without such a system, middle sheath 12 may be inadvertently retracted before outer sheath 11, rendering the delivery catheter inoperable.

This aspect of the invention also allows the physician to perform only a single, uninterrupted motion to deploy the prosthesis. This helps prevent deployment errors by allowing the physician to devote more attention to other aspects of the procedure. Rather than performing a first retraction motion, removing a lock (for example), and then performing a second retraction motion, only a single motion is required.

Figure 4:
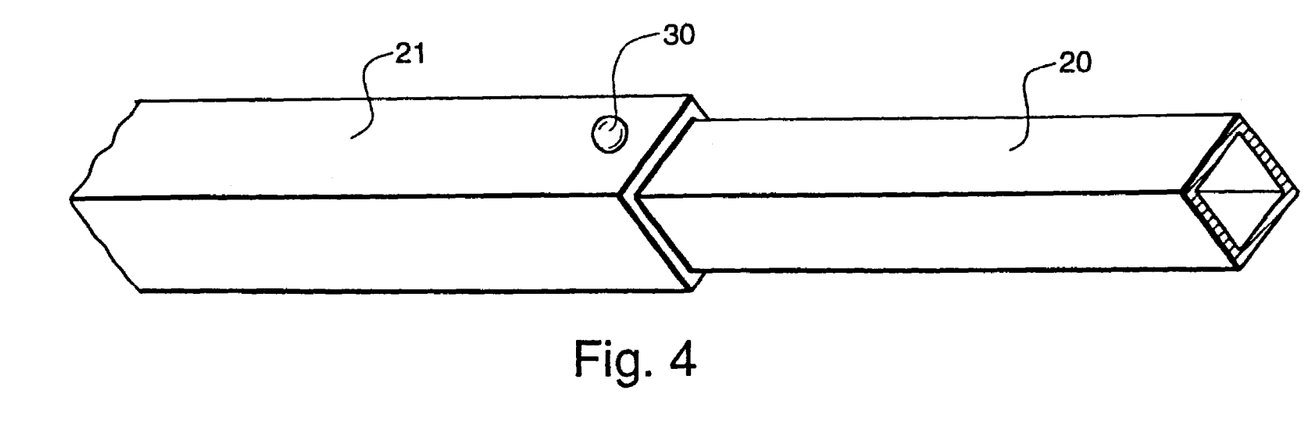
FIG. 4 is a isometric view of a portion of another exemplary multi-sheath delivery catheter according to this invention.

Sheath sequencing is achieved according to this aspect of the invention in combination with either an internal or an external locking mechanism, or a combination of internal and external mechanisms, that lock adjacent tubes to one another to prevent relative axial movement until the tubes are unlocked from one another. FIGS. 4 and 5 illustrate a first embodiment of this aspect of the invention. In this embodiment, the frictional forces between pusher 13 and middle sheath 12 (and their associated handles), and between middle sheath 12 and the prosthesis, are sufficient to prevent undesirable sliding of middle sheath 12 over pusher 13 as outer sheath 11 is being retracted.

FIG. 4 shows the portion of the catheter of this invention where handle 20 attached to pusher 13 extends out of handle 21 attached to middle-sheath 12. Handle 21 has a protrusion 30 on its outer surface. During deployment, outer sheath 11 (FIG. 5) is retracted over middle sheath 12 and associated tube 21 to deploy a first portion of a prosthesis. During this retraction of outer sheath 11, the frictional forces between middle sheath 12 and pusher 13 and between middle sheath 12 and the prosthesis are sufficient to prevent any relative axial motion between them.

According to this aspect of the invention, non-round portion 31 of the inner surface of outer sheath 11 is positioned such that upon deployment of the first portion of the prosthesis, portion 31 (which itself is effectively a protrusion from the inner surface of outer sheath 11) of outer sheath 11 engages protrusion 30 on the outer surface of handle 21. By virtue of this engagement, the physician can overcome the frictional forces between pusher 13 and middle tube 12, and between middle sheath 12 and the prosthesis, by continuing to retract outer sheath 11. This causes relative motion between middle sheath 12 and pusher 13. As a result, both outer sheath 11 and middle sheath 12 are retracted simultaneously after the engagement of portion 31 with protrusion 30 to complete deployment of the endoluminal prosthesis.

Single motion sequenced retraction is thus achieved using this aspect of the invention. The physician need only retract one tube (outer sheath 11) and proper sequenced tube retraction is automatically ensured using by virtue of the engagement of portion 31 and protrusion 30.

Figure 6:
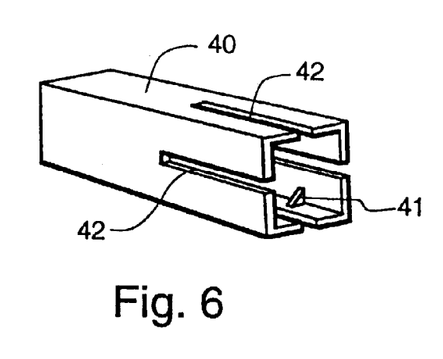
FIG. 6 is a isometric view of a component used in another exemplary multi-sheath delivery catheter according to this invention.
Figure 6A:
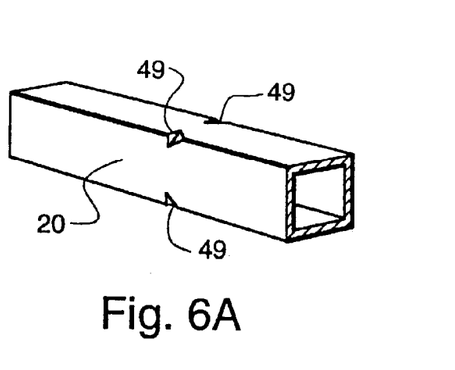
FIG. 6A is a isometric view of a portion of an exemplary multi-sheath delivery catheter according to this invention.
Figure 7:
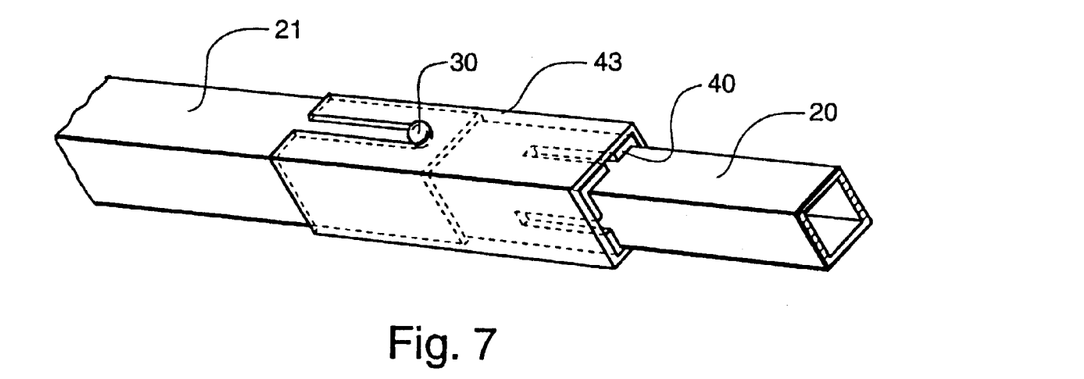
FIG. 7 is a isometric view of a portion of an exemplary multi-sheath delivery catheter according to this invention.
Figure 8:
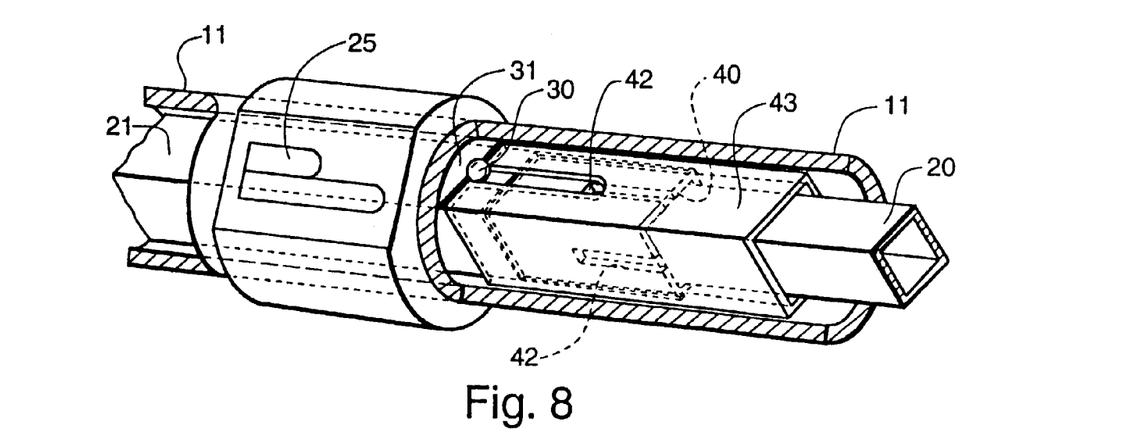
FIG. 8 is a partially cut-away isometric view of a portion of an exemplary multi-sheath delivery catheter according to this invention.

FIGS. 6–8 illustrate sequenced sheath retraction using a separate prong assembly 40 as an internal lock mechanism in the event that the frictional forces between the tubes is not sufficient to prevent undesirable relative axial movement. As shown in FIG. 6, a prong assembly 40, formed of a thermoplastic material such as polyethylene, or of stainless steel, or of other suitable material, has a cross-sectional profile that matches that of handle 20. Prong assembly 40 is adapted to be disposed around the periphery of handle 20. Prong assembly 40 has slits 42 formed in the sides thereof and prongs 41 disposed in each inside corner thereof in the illustrated embodiment. As shown in FIG. 6A, notches 49 are formed in the corners of handle 20. Prongs 41 of the prong assembly 40 are adapted to fit into notches 49 when prong assembly 40 is disposed on handle 20.

FIG. 7 illustrates the use of prong assembly 40 in accordance with an exemplary embodiment of this aspect of this invention. Prong assembly 40 is placed on handle 20 attached to pusher 13 such that prongs 41 fit into notches 49. A lock ring 43 is then placed over both prong assembly 40 and a distal portion of handle 21 attached to middle sheath 12. Lock ring 43 serves to maintain the engagement of prongs 41 with notches 49 in handle 20. Absent lock ring 43, prongs 41 are easily disengaged from notches 49. Lock ring 43 includes a slot 44 which is adapted to allow protrusion 30 in tubular handle 21 to remain uncovered and to slide relative to lock ring 43 as lock ring 43 is retracted off handle 21 as described below. In the configuration illustrated in FIG. 7, middle sheath 12 is locked from retracting relative to pusher 13 because handle 21 cannot slide over the locked prong assembly 40 attached to handle 20. This prevents relative movement between middle sheath 12 and pusher 13.

Lock ring 43 preferably has two portions of separate cross-sectional areas. The larger cross-sectional area portion is disposed over the periphery of handle 21, and the smaller cross-sectional area portion is disposed over the periphery of prong assembly 40. Both prong assembly 40 and lock ring 43 must have a wall thickness such that they will fit easily within outer sheath 11.

FIG. 8 illustrates the use of this internal locking mechanism during deployment of a prosthesis according to an embodiment of this invention wherein the mechanism is used in combination with the sequenced sheath retraction aspect of the invention described above. Outer sheath 11 is retracted until the first, larger diameter portion of the prosthesis is deployed. At that point, the distal end of portion 31 has engaged the proximal end of lock ring 43 and pushed the small diameter portion of lock ring 43 off prong assembly 40. Because the large diameter portion of lock ring 43 now covers prong assembly 40, there is no forced engagement of prongs 41 with notches 49 (the large diameter portion of lock ring 43 being sized such that there is space for prongs 41 to become disengaged within the large diameter portion of lock ring 43). Prongs 41 are thus released from notches 49 in handle 20. Middle sheath 12 is thus unlocked from pusher 13, and these two portions of the catheter can move relative to one another. Also at this point during retraction, portion 31 engages protrusion 30 on handle 21, causing the sequenced sheath retraction described above.

Figure 9:
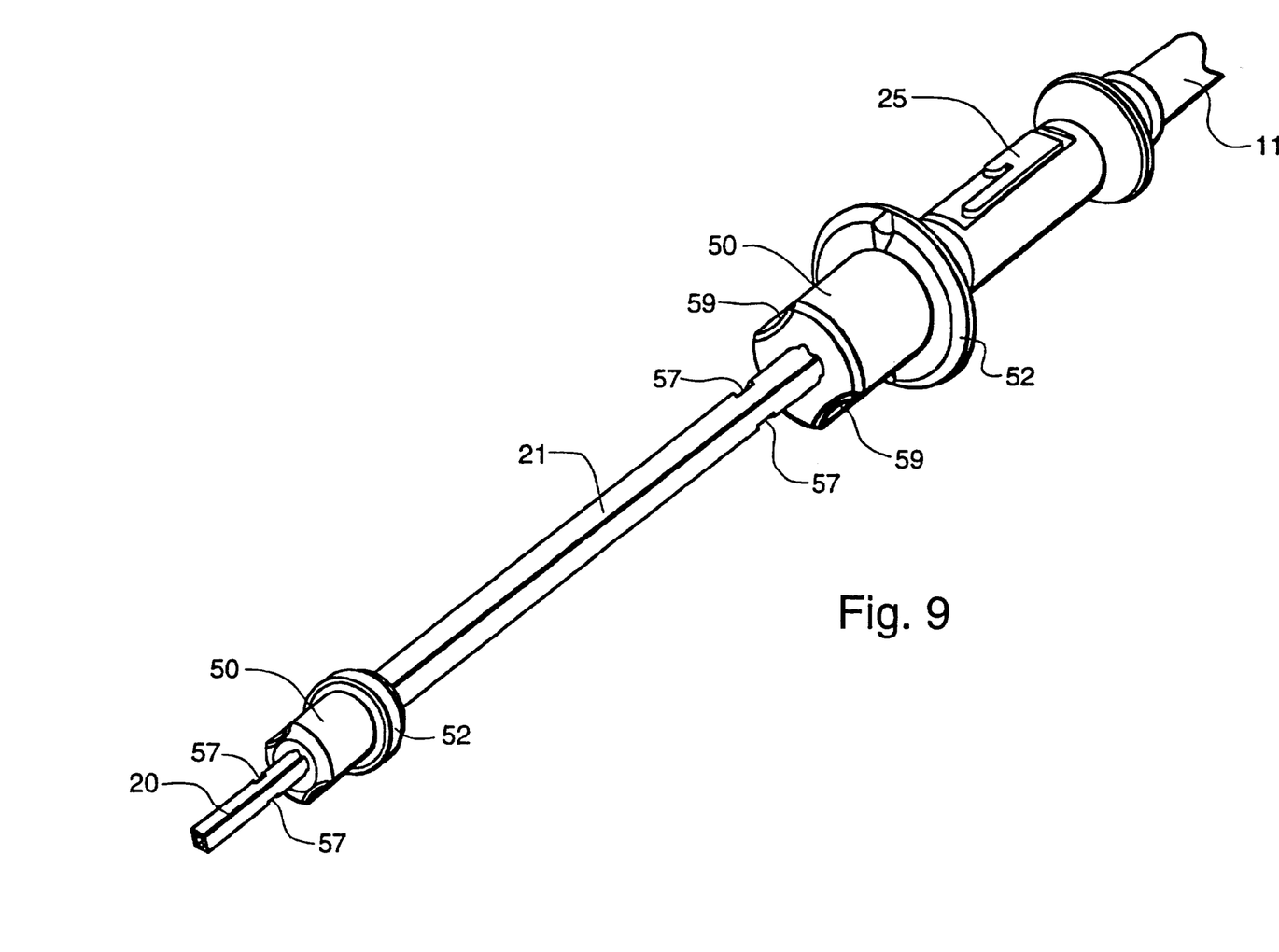
FIG. 9 is a isometric view of another exemplary multi-sheath delivery catheter according to this invention.

FIG. 9 illustrates another embodiment of this aspect of the invention for locking tubes together to prevent axial movement relative to one another. FIG. 9 shows an assembled catheter according to this invention where the distal end of handle 20 protrudes from the distal end of handle 21, which in turn protrudes from the outer end of outer sheath 11, which extends into the body of a patient into whom a prosthesis is to be inserted. In this embodiment, cam lock assemblies 50 are disposed at the portions of the catheter where one tube protrudes from another. Cam lock assemblies 50 allow locking and unlocking of the tube from which another tube protrudes and the protruding tube (generally referred to as an outer tube and an inner tube).

Figure 10:
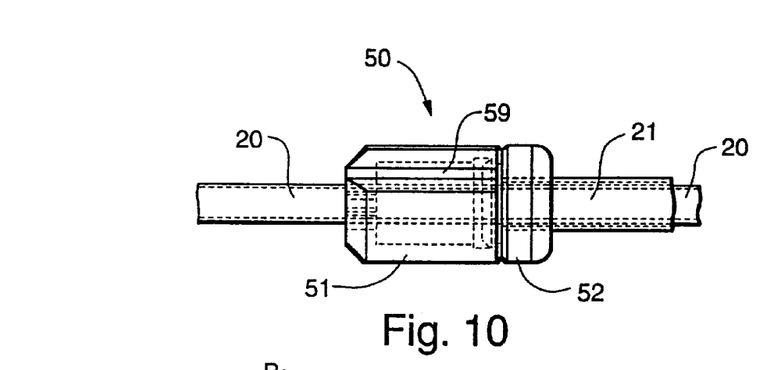
FIG. 10 is a side view of a portion of the exemplary multi-sheath delivery catheter illustrated in FIG. 9.

FIG. 10 is a side view of one of the cam-lock assemblies 50. Although illustrated and described in connection with the locking and unlocking of handles 20 and 21 (and hence pusher 13 and middle sheath 12), any of the adjacent tubes may be locked and unlocked using the cam-lock assembly design described below.

As shown in FIG. 10, cam-lock assembly 50 includes a cam lock knob 51 and a hub 52. Cam-lock knob 51 is attached to, and pivots on, hub 52 which is glued or press-fit (or otherwise fixedly mounted) onto the distal end of handle 21.

Figure 11:
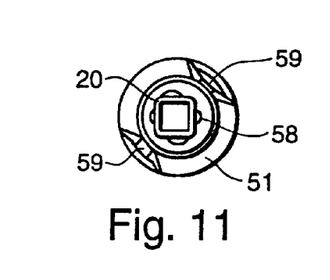
FIG. 11 is an end view of the portion of the exemplary multi-sheath delivery catheter shown in FIG. 10.

FIG. 11 is an end view of the cam-lock assembly 50 shown in FIG. 10. As illustrated in FIG. 11 (and in FIG. 9) cam-lock assembly 50 includes indents 59 provided for easy handling and gripping by a physician using the device to insert a prosthesis. Also as shown in FIG. 11, and as shown in detail in FIG. 12, cam-lock knob 51 has a detailed inner cam surface 58 that allows respective engagement and disengagement of cam-knob 51 with notches 57 formed in handle 20.

Figure 12:
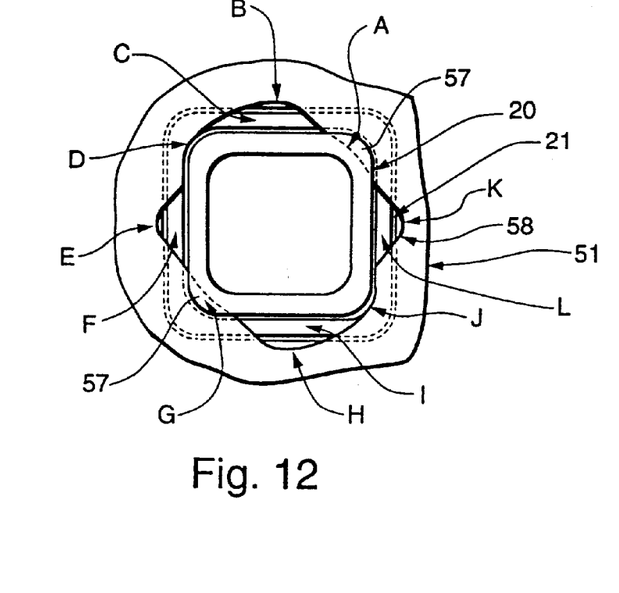
FIG. 12 is a sectional detail view of a portion of the multi-sheath delivery catheter illustrated in FIG. 11.

In the situation illustrated in FIG. 12, inner surface 58 of cam-lock knob 51 extends into notch 57 at A. Inner cam surface 58 then extends out away from handle 20 at B, creating an open space C between inner cam surface 58 and handle 20. Inner cam surface 58 then contours to the corner of handle 20 at D, extends away from handle 20 at E, creating inner space F, then extends into notch 57 in handle 20 at G, extends back out away from handle 20 at H, creating space I, contours around another corner of handle 20 at J, and extends away from handle 20 at K, creating space L.

By virtue of inner cam surface 58 extending into the notches 57 of handle 20 at points A and G, handles 20 and 21 (and hence pusher 13 and middle sheath 12) are prevented from axial movement relative to one another.

Figure 13:
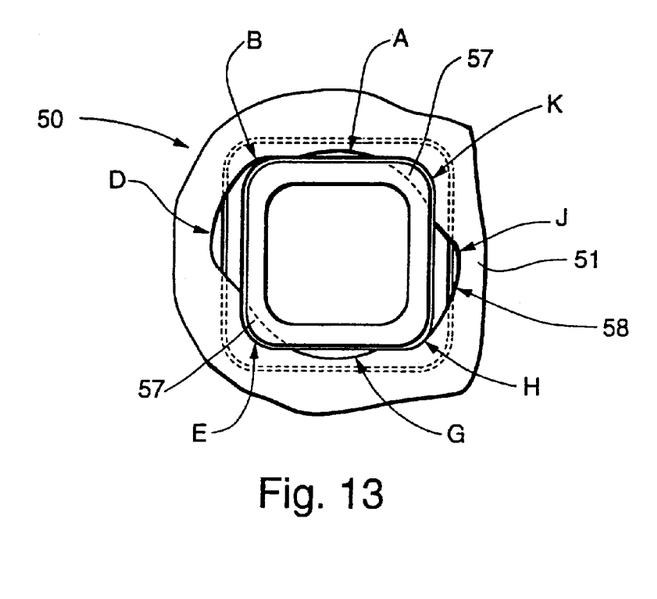
FIG. 13 is a sectional detail view of the exemplary multi-sheath delivery catheter shown in FIG. 11.

To unlock cam-lock assembly 50 and allow relative movement between tubes 20 and 21, cam lock assembly 51 is rotated by a physician (for example) 45° counter clockwise from the illustration shown in FIG. 12. The result is the situation illustrated in FIG. 13. Inner surface 58 of cam-lock knob 51 in FIG. 13 is contoured such that no part of inner surface 58 extends into notches 57 of handle 20. Corresponding lettered points along inner surface 58 are shown in FIG. 13 relative to their position in FIG. 12. As can be seen, each lettered point has rotated 45° counter clockwise such that there is no engagement with notches 57 of handle 20. Accordingly, handle 20 is free to slide axially relative to handle 21, and hence pusher 13 can move axially relative to middle sheath 12.

Using cam-lock assembly 50, middle sheath 12 and pusher 13 may be selectively rigidly fixed and unlocked with respect to one another. The illustrated embodiment shows handles 20 and 21 having the same cross-sectional shape, but cam-lock assembly 50 can be used when the cross sectional shapes are different. The locking function of cam-lock assembly 50 is accomplished by the detailed inner cam surface 58 of cam-lock knob 51 which, when locked, engages premachined notches 57 in handle 20. When cam-lock knob 51 is in the locked position, the two handles 20 and 21 cannot move axially, or slide, relative to one another. Cam-lock assembly 50 becomes unlocked when cam-lock knob 51 is turned counter clockwise approximately 45° in this embodiment, thereby disengaging inner cam surface 58 from notches 57 in inner tubing 20.

Cam-lock knob assembly 50 provides several advantages. First, handles 20 and 21 may be rigidly locked with absolutely no axial motion relative to one another by non-frictional means. This is important in an operating environment where contact with bodily fluids could easily disable frictional locking devices by reducing the coefficient of friction. Thus, accidental unlocking of the device is very unlikely. Second, cam-lock assembly 50 has a "positive feel" in both the locked and unlocked positions and is not easily placed in an intermediate position. Cam-lock knob assembly 50 may be a semi-rigid thermoplastic material, and handles 20 and 21 may be thermoplastic or metallic material, which allows slight deformations of cam-lock knob 50 to provide user feedback with a click or snap when locked. This, along with visual confirmation, lets the user, typically a physician, know whether the device is locked or not. Third, cam-lock assembly 50 is easy to use and intuitive, which is critical to the physician operating the device. Cam lock knob 51 may also be manufactured with a large grip to provide grip for gloved hands. The intuitive clockwise-lock and counter clockwise-unlock motions are nearly universal and describe a vast majority of screws and fasteners. Lastly, cam-lock assembly 50 has the ability to lock handle 20 in more than one position if multiple sets of notches 57 are provided. This may be useful when deploying different sizes of prostheses, for example. Notches 57 in handle 20 may be machined, by methods known to those skilled in the art, before the device is assembled. Notches 57 may also be molded instead of machined, or cut after assembly but before locking.

According to another aspect of this invention, a seal may be provided between outer sheath 11 and middle sheath 12 and between middle sheath 12 and pusher 13. Such a seal is desired, for example, to prevent saline solution from leaking out of the catheter during flushing of the device to remove air bubbles. The sealing also prevents blood from escaping from the catheter when it is inserted into the patient's body.

Figure 14:
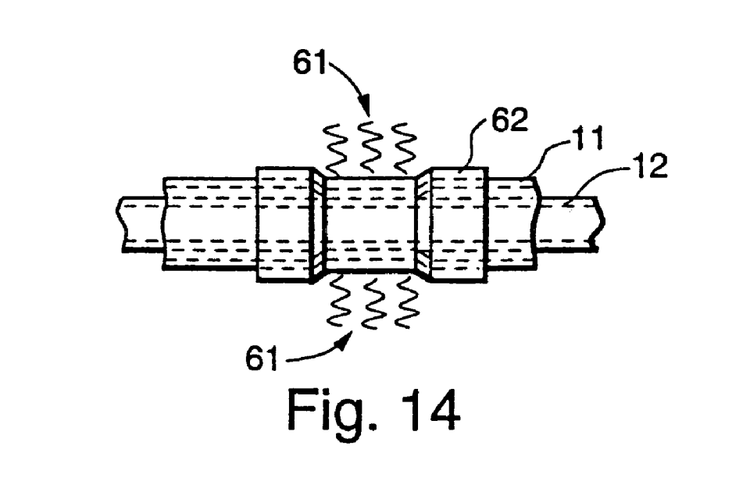
FIG. 14 is a side view of a portion of another exemplary multi-sheath delivery catheter according to this invention.

The seal is created by applying a radial compressive force to the periphery of an outer tube while heating it over an inner tube or an appropriately sized mandrel. FIG. 14 illustrates the use of a Teflon heat shrink tubing 60 to provide the radial compressive force during heating (heat illustrated at 61), which is typically done with a heat gun or a lap-welder. As shown in FIG. 14, tubing 60 is applied over outer sheath 11 which has middle sheath 12 (as opposed to a mandrel) disposed within it. As will be understood by those skilled in the art, the heating should be of sufficient time and temperature (for example, 450° degrees F. for 15 seconds) to allow softening of the thermoplastic material of which the outer tube is formed in order to allow it to form a seal with the inner tube as tubing 60 shrinks.

Figure 14A:
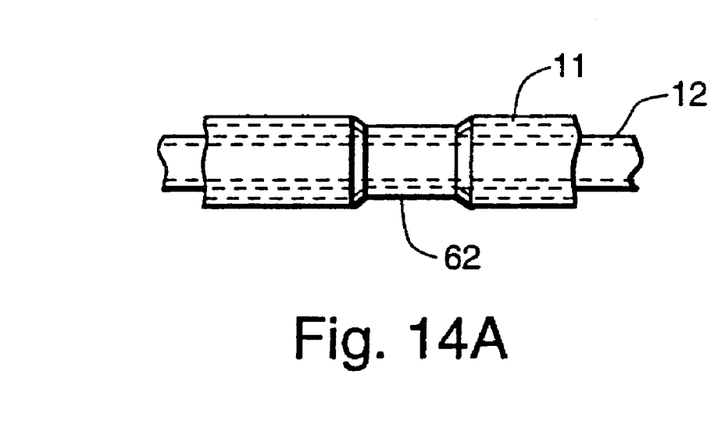
FIG. 14A is a side view of a portion of another exemplary multi-sheath delivery catheter according to this invention.

Forming a seal in this manner creates a local region 62 (the region where tubing 60 and heat 61 are applied) where the inside diameter of outer sheath 11 is very closely sized to the outer diameter of outer sheath 12. As shown in FIG. 14A, this creates the desired seal. The same technique may be used to form a seal between middle sheath 12 and pusher 13 contained within it.

This aspect of the invention provides an efficient, reliable seal between the respective parts of the catheter. This is an improvement over simply attempting to manufacture the sheaths of appropriately sized dimensions. Extrusion, or other formation, to such precise dimensions throughout the entire length of the sheaths is not feasible. Because of manufacturing variations, the tubes would either be too loose (no sealing) or too tight (excessive sliding friction). This invention overcomes these manufacturing and use limitations.

Figure 15:
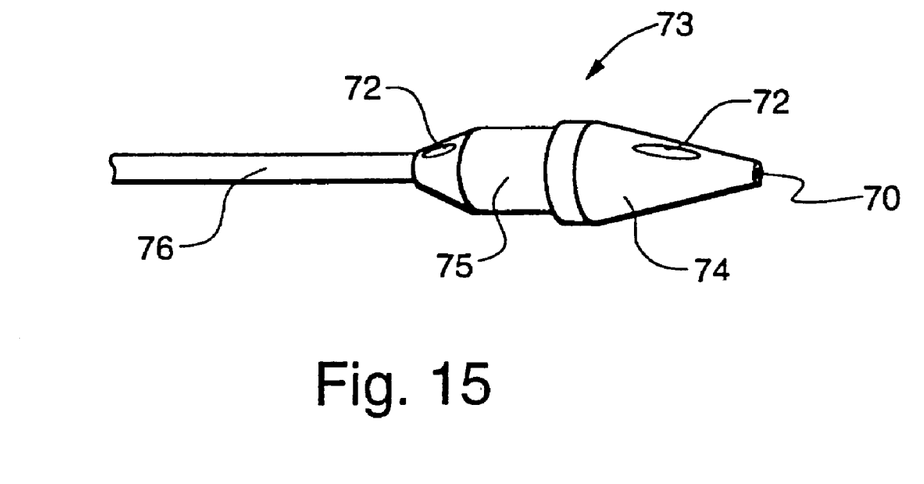
FIG. 15 is a side view of a portion of another exemplary multi-sheath delivery catheter according to this invention.

According to another aspect of the invention illustrated in FIG. 15, a guide tip 73 with a through-hole 70 for a guidewire is connected to an inner shaft 76 to be contained within pusher 13 of the catheter of this invention. Passage of the guide tip 73 followed by the remainder of the catheter is facilitated by tracking over a guidewire previously introduced into the vessel.

Guide tip 73 is formed of a thermoplastic material, preferably flexible. Front portion 74 of guide tip 73 extends proximally out from outer sheath 11 (not shown), while back portion 75 is contained within outer sheath 11. A through-hole 72 is formed in guide tip 73. Through-hole 72 provides fluid communication between the inside of outer sheath 11 and the environment.

Figure 16:
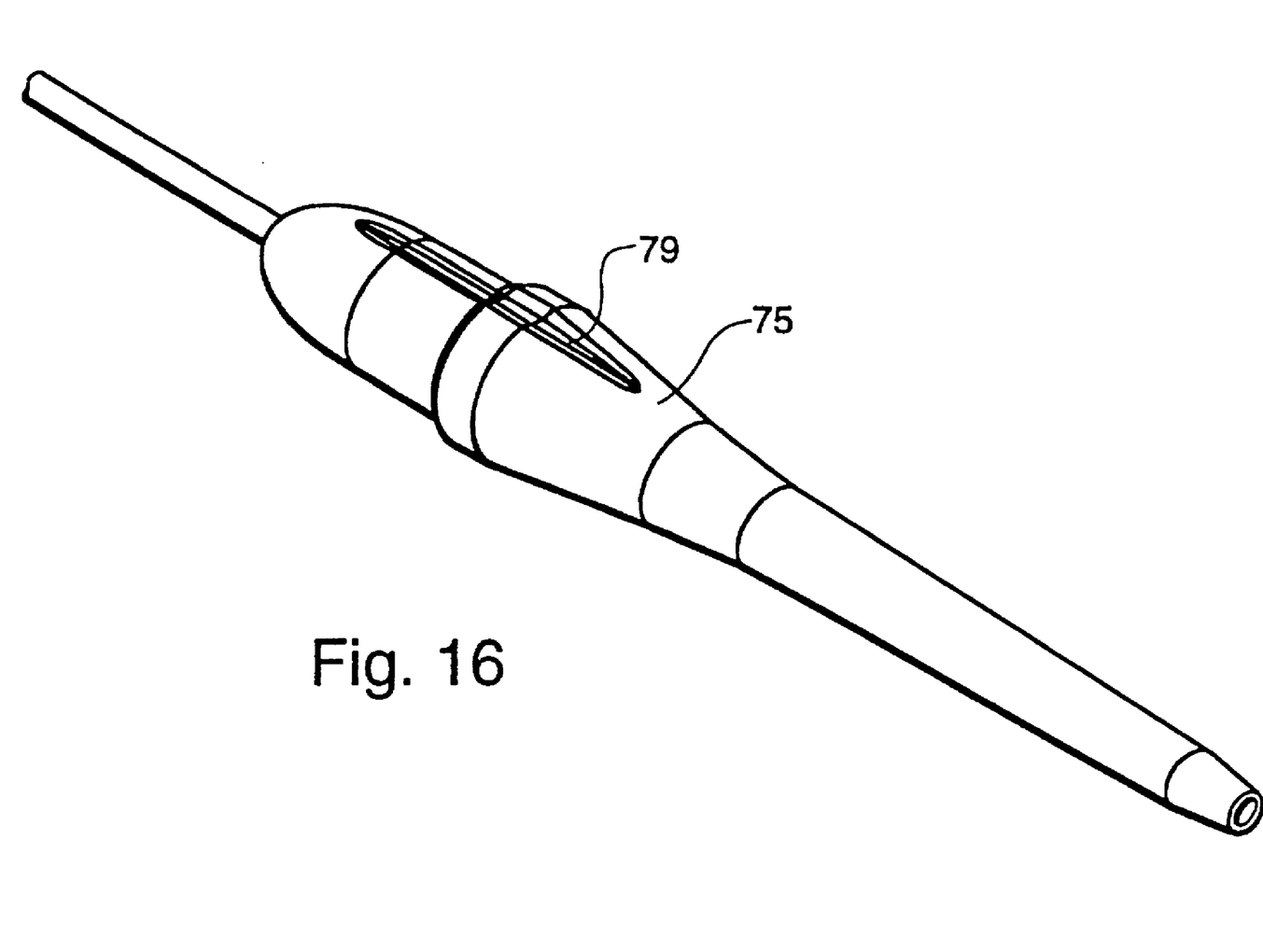
FIG. 16 is a side view of a portion of another exemplary multi-sheath delivery catheter according to this invention.

When the fully assembled catheter is ready for insertion into a patient, immediately before use, the system is typically flushed with saline solution to remove air from the catheter and prosthesis. Through-hole 72 allows the saline solution to be ejected from the inside of outer sheath 11 to the environment to insure that the air is removed. Rather than through-hole 72, a groove 79 may be used for the same purpose as shown in the alternative embodiment illustrated in FIG. 16.

Although this invention has been described in connection with certain specific embodiments, the scope of the invention is not intended to be limited thereto.

The invention claimed is:

1. A delivery catheter for introducing a prosthesis into a body lumen, the delivery catheter comprising a plurality of sequentially retractable nested sheaths for deploying the prosthesis, the nested sheaths comprising an outer sheath having a first member located on an inner surface of the outer sheath and an inner sheath having a second member located on an outer surface of the inner sheath, the outer sheath containing a first discrete portion of the prosthesis and the inner sheath containing a second discrete portion of the prosthesis, the outer sheath adapted to be retracted in a path over the inner sheath until a point at which the first member engages the second member such that further retraction of the outer sheath causes simultaneous retraction of the inner sheath.

2. The delivery catheter of claim 1, wherein the first member and the second member each comprise a protrusion from the respective surface of the sheath.

3. The delivery catheter of claim 1, wherein the inner sheath is nested concentrically within the outer sheath.

4. The delivery catheter of claim 1 further comprising a pusher slideably disposed at least partly within the inner sheath and adapted to engage at least one portion of the prosthesis.

5. The delivery catheter of claim 1, further comprising a nose cone at one end of the catheter, the nose cone comprising an air removal port for flushing the catheter and prosthesis to remove air before insertion into the body lumen.

6. The delivery catheter of claim 5, wherein the air removal port comprises a through-hole.

7. The delivery catheter of claim 1 further comprising a seal between the inner sheath and the outer sheath for minimizing leakage of fluid from the catheter.

8. The delivery catheter of claim 7, wherein the seal comprises a reduced diameter portion of the outer sheath having an inside diameter nearly equivalent to an outside diameter of the inner sheath.

9. The delivery catheter of claim 1, wherein the catheter further comprises a visual indicator illustrating orientation of the prosthesis within the catheter.

10. A delivery catheter for introducing a prosthesis into a body lumen, the delivery catheter comprising a plurality of sequentially retractable nested sheaths for deploying the prosthesis, at least one of the nested sheaths adapted to contain at least a portion of the prosthesis, the nested sheaths comprising an outer sheath having a first member located on an inner surface of the outer sheath and an inner sheath having a second member located on an outer surface of the inner sheath, the outer sheath adapted to be retracted in a path over the inner sheath until a point at which the first member engages the second member such that further retraction of the outer sheath causes simultaneous retraction of the inner sheath, the delivery catheter further comprising an anti-rotation element for preventing relative rotation between the inner sheath and the outer sheath.

11. A delivery catheter for introducing a modular prosthesis into a body lumen, the delivery catheter comprising a plurality of sequentially retractable nested sheaths for deploying the prosthesis, the nested sheaths comprising an outer sheath having a first member, an inner sheath having a second member, and an anti-rotation element for preventing relative rotation between the inner sheath and the outer sheath, the outer sheath containing a first discrete modular portion of the prosthesis and the inner sheath containing a second discrete modular portion of the prosthesis, the outer sheath adapted to be retracted in a path over the inner sheath until a point at which the first member engages the second member such that further retraction of the outer sheath causes simultaneous retraction of the inner sheath.

12. The delivery catheter of claim 11, wherein the prosthesis second portion has a desired rotational alignment with the prosthesis first portion, the prosthesis second portion disposed within the inner sheath in the desired rotational alignment; the delivery catheter adapted to maintain the desired rotational alignment during introduction of the delivery catheter into the body lumen and deployment of the prosthesis in a deployment location.

13. The delivery catheter of claim 12, wherein the sequentially retractable nested sheaths are adapted to facilitate deployment of the first portion and the second portion of the modular prosthesis in a single, uninterrupted motion and the anti-rotation element is adapted to minimize twisting of the prosthesis within the delivery catheter.

14. The delivery catheter of claim 12, wherein the catheter further comprises a visual indicator illustrating orientation of the prosthesis within the catheter.

15. The delivery catheter of claim 11, wherein the inner sheath is nested concentrically within the outer sheath.

16. The delivery catheter of claim 11 further comprising a pusher slideably disposed at least partly within the inner sheath and adapted to engage at least one portion of the prosthesis.

17. The delivery catheter of claim 11, further comprising a nose cone at one end of the catheter, the nose cone comprising an air removal port for flushing the catheter and prosthesis to remove air before insertion into the body lumen.

18. The delivery catheter of claim 11, wherein the catheter further comprises a visual indicator illustrating orientation of the prosthesis within the catheter.

19. A delivery catheter for introducing a prosthesis into a body lumen, the delivery catheter comprising a plurality of sequentially retractable nested sheaths for deploying the prosthesis, at least one of the nested sheaths adapted to contain at least a portion of the prosthesis, the nested sheaths comprising an outer sheath having a first member located on an inner surface of the outer sheath and an inner sheath having a second member located on an outer surface of the inner sheath, the outer sheath adapted to be retracted in a path over the inner sheath until a point at which the first member engages the second member such that further retraction of the outer sheath causes simultaneous retraction of the inner sheath, the delivery catheter further comprising a pusher slideably disposed at least partly within the inner sheath and adapted to engage at least one portion of the prosthesis, and an anti-rotation element for preventing relative rotation between the pusher and the inner sheath.

20. The delivery catheter of claim 19, wherein the outer sheath is adapted to contain a first portion of the prosthesis and the inner sheath is adapted to contain a second portion of the prosthesis.

21. A delivery catheter for introducing a prosthesis into a body lumen, the delivery catheter comprising a plurality of sequentially retractable nested sheaths for deploying the prosthesis, one or more of the nested sheaths adapted to contain at least a portion of the prosthesis, the nested sheaths comprising an outer sheath having a first member, an inner sheath having a second member, and an anti-rotation element for preventing relative rotation between the inner sheath and the outer sheath, the anti-rotation element comprising (a) at least a portion of the outer sheath having a non-round cross-section, and (b) a first handle connected to the inner sheath and having at least a portion with a non-round cross-section corresponding to and adapted to engage the non-round cross-section portion of the outer sheath, the outer sheath adapted to be retracted in a path over the inner sheath until a point at which the first member engages the second member such that further retraction of the outer sheath causes simultaneous retraction of the inner sheath.

22. The delivery catheter of claim 21, wherein the non-round cross-section portions of each of the outer sheath and the first handle have a shape selected from the group consisting of: square, rectangular, triangular, ovular, creased, flattened and D-shaped.

23. The delivery catheter of claim 21, wherein the portion of the outer sheath having the non-round cross-section comprises a separate member attached to the outer sheath.

24. The delivery catheter of claim 21, wherein the portion of the outer sheath having the non-round cross-section is an integral portion of the outer sheath.

25. The delivery catheter of claim 21, wherein the first handle is integrally connected to the inner sheath.

26. The delivery catheter of claim 21, wherein the first handle comprises a separate member attached to the inner sheath.

27. The delivery catheter of claim 21, wherein the outer sheath is adapted to contain a first portion of the prosthesis and the inner sheath is adapted to contain a second portion of the prosthesis, the delivery catheter further comprising a pusher slideably disposed at least partly within the inner sheath and adapted to engage at least one portion of the prosthesis, the pusher comprising a second handle, the second handle comprising at least a portion having a non-round cross-section adapted to engage the non-round cross-section portion of the first handle.

28. The delivery catheter of claim 27, wherein the non-round cross-section portions of each of outer sheath, the first handle, and the second handle have a non-round cross-section having a shape selected from the group consisting of: square, rectangular, triangular, ovular, creased, flattened, and D-shaped.

29. The delivery catheter of claim 27, wherein the second handle is integrally connected to the pusher.

30. The delivery catheter of claim 27, wherein the second handle comprises a separate member attached to the pusher.

31. A delivery catheter for introducing a prosthesis into a body lumen, the delivery catheter comprising a plurality of sequentially retractable nested sheaths for deploying the prosthesis, at least one of the nested sheaths adapted to contain at least a portion of the prosthesis, the nested sheaths comprising an outer sheath having a first member located on an inner surface of the outer sheath and an inner sheath having a second member located on an outer surface of the inner sheath, the outer sheath adapted to be retracted in a path over the inner sheath until a point at which the first member engages the second member such that further retraction of the outer sheath causes simultaneous retraction of the inner sheath, the delivery catheter further comprising a nose cone at one end of the catheter, the nose cone comprising an air removal port for flushing the catheter and prosthesis to remove air before insertion into the body lumen, wherein the air removal port comprises a groove.

32. A delivery catheter for introducing a prosthesis into a body lumen, the delivery catheter comprising a plurality of sequentially retractable nested sheaths for deploying the prosthesis, at least one of the nested sheaths adapted to contain at least a portion of the prosthesis, the nested sheaths comprising an outer sheath having a first member, an inner sheath having a second member, and a seal between the inner sheath and the outer sheath comprising a reduced diameter portion of the outer sheath having an inside diameter nearly equivalent to an outside diameter of the inner sheath for minimizing leakage of fluid from the catheter, the outer sheath adapted to be retracted in a path over the inner sheath until a point at which the first member engages the second member such that further retraction of the outer sheath causes simultaneous retraction of the inner sheath, the reduced diameter portion of the outer sheath comprising a portion created by a process comprising the steps of:
  (a) applying a compressive force to a normal diameter portion of the outer sheath that is disposed over the inner sheath; and
  (b) heating the outer sheath to shrink the outer sheath around the inner sheath.

33. The delivery catheter of claim 32, wherein the step of applying the compressive force comprises using heat shrink tubing over the outer sheath.

34. A delivery catheter for introducing a prosthesis into a body lumen, the delivery catheter comprising a plurality of sequentially retractable nested sheaths for deploying the prosthesis, at least one of the nested sheaths adapted to contain at least a portion of the prosthesis, the nested sheaths comprising:
  an outer sheath having a first member,
  an inner sheath having a second member,
  a pusher slideably disposed at least partly within the inner sheath and adapted to engage at least one portion of the prosthesis,
  a first seal between the inner sheath and the outer sheath, and
  a second seal between the inner sheath and the pusher,
  the first seal and the second seal for minimizing leakage of fluid from the catheter, the outer sheath adapted to be retracted in a path over the inner sheath until a point at which the first member engages the second member such that further retraction of the outer sheath causes simultaneous retraction of the inner sheath.

35. The delivery catheter of claim 34, wherein the first seal comprises a reduced diameter portion of the outer sheath having an inside diameter nearly equivalent to the outside diameter of the inner sheath, and the second seal comprises a reduced diameter portion of the inner sheath having an inside diameter nearly equivalent to the outside diameter of the pusher.

36. The delivery catheter of claim 35, wherein the reduced diameter portions of the inner sheath and the outer sheath comprise portions created by a process comprising the steps of:

(a) applying a compressive force to a normal diameter portion of the inner sheath that is disposed over the pusher;
(b) heating the inner sheath to shrink the inner sheath around the pusher;
(c) applying a compressive force to a normal diameter portion of the outer sheath that is disposed over the inner sheath; and
(d) heating the outer sheath to shrink the outer sheath around the inner sheath.

37. The delivery catheter of claim 36, wherein the step of applying the compressive force to the inner sheath comprises using heat shrink tubing over the inner sheath and the step of applying the compressive force to the outer sheath comprises using heat shrink tubing over the outer sheath.

38. The delivery catheter of claim 34, further comprising a nose cone at one end of the catheter, the nose cone comprising an air removal port for flushing the catheter and prosthesis to remove air before insertion into the body lumen.

39. The delivery catheter of claim 34, wherein the catheter further comprises a visual indicator illustrating orientation of the prosthesis within the catheter.

40. A delivery catheter for introducing a prosthesis into a body lumen, the delivery catheter comprising a plurality of sequentially retractable nested sheaths for deploying the prosthesis, one or more of the nested sheaths adapted to contain at least a portion of the prosthesis, the nested sheaths comprising an outer sheath having a first member, an inner sheath having a second member, an anti-rotation element for preventing relative rotation between the inner sheath and the outer sheath, and a seal between the inner sheath and the outer sheath for minimizing leakage of fluid from the catheter, the seal comprising a reduced diameter portion of the outer sheath having an inside diameter nearly equivalent to an outside diameter of the inner sheath, the outer sheath adapted to contain a first portion of the prosthesis and the inner sheath adapted to contain a second portion of the prosthesis, the outer sheath adapted to be retracted in a path over the inner sheath until a point at which the first member engages the second member such that further retraction of the outer sheath causes simultaneous retraction of the inner sheath.

* * * * *

UNITED STATES PATENT AND TRADEMARK OFFICE
CERTIFICATE OF CORRECTION

PATENT NO. : 7,022,133 B2
APPLICATION NO. : 10/457183
DATED : April 4, 2006
INVENTOR(S) : Carl E. Yee et al.

It is certified that error appears in the above-identified patent and that said Letters Patent is hereby corrected as shown below:

On The Title Page Item -75-, Inventors... "Thomas Roberts" should read --George T. Roberts-- "Frank Occidentale" should read -- Frank A. Occidentale-- and "Robert Christie" should read -- Robert A. Christie--.

On The Title Page, Item -57-, line 12, Abstract..." A multi-sheath delivery catheter and method for introducing a prosthesis into a body lumen involving use of (a) an outer sheath adapted to contain a portion of the prosthesis and having an inner surface with a non-round cross-section; (b) a middle sheath slideably disposed at least partly within the outer sheath and adapted to contain another portion of the prosthesis, the middle sheath having a distal end with a first handle attached to it that has a non-round cross-section corresponding to and engaging the non-round cross-section of the inner surface of the outer sheath; and (c) a pusher slideably disposed at least partly within the middle sheath and adapted to engage the prosthesis, relative rotational movement between the outer sheath and the middle sheath is prevented by virtue of the engagement of the non-round cross-section of the first handle with the non-round cross-section of the inner surface of the outer sheath. The delivery catheter has a mechanism for sequentially retracting concentric tubes to deploy the prosthesis." should read --A delivery catheter for deploying a prosthesis in a body lumen and comprising a plurality of sequentially retractable nested sheaths, including at least an outer sheath and an inner sheath, at least one of which is adapted to contain a portion of the prosthesis. The outer sheath retracts over the inner sheath until a first member on the outer sheath engages a second member on the inner sheath, after which the sheaths retract together. The delivery catheter may further comprise an anti-rotation element for preventing relative rotation between the inner and outer sheaths, a nose cone at one end of the catheter with an air removal port for flushing the catheter, and/or a visual indicator to illustrate orientation of the prosthesis within the catheter. A seal between the inner and outer sheaths may be provided to minimize leakage of fluid from the catheter.--

Signed and Sealed this

Nineteenth Day of June, 2007

JON W. DUDAS
*Director of the United States Patent and Trademark Office*